(12) United States Patent
Guminski et al.

(10) Patent No.: US 8,148,552 B2
(45) Date of Patent: Apr. 3, 2012

(54) PROCESS FOR THE SYNTHESIS OF ANTICANCER (POLY) AMINOALKYLAMINOACETAMIDE DERIVATIVES OF EPIPODOPHYLLOTOXIN

(75) Inventors: Yves Guminski, Lagarrigue (FR); Martial Grousseaud, Castres (FR); Thierry Imbert, Viviers les Montagnes (FR)

(73) Assignee: Pierre Fabre Medicament, Boulogne Billancourt (FR)

( * ) Notice: Subject to any disclaimer, the term of this patent is extended or adjusted under 35 U.S.C. 154(b) by 147 days.

(21) Appl. No.: 12/733,862

(22) PCT Filed: Sep. 23, 2008

(86) PCT No.: PCT/FR2008/051697
§ 371 (c)(1), (2), (4) Date: Mar. 24, 2010

(87) PCT Pub. No.: WO2009/050363
PCT Pub. Date: Apr. 23, 2009

(65) Prior Publication Data
US 2010/0280263 A1        Nov. 4, 2010

(30) Foreign Application Priority Data
Sep. 25, 2007 (FR) .................. 07 06692

(51) Int. Cl.
*C07D 307/77* (2006.01)

(52) U.S. Cl. ....................................... 549/298
(58) Field of Classification Search ............ 549/298
See application file for complete search history.

(56) References Cited

FOREIGN PATENT DOCUMENTS

| SU | 598871 | 3/1978 |
|---|---|---|
| WO | WO 97/21713 | 6/1997 |
| WO | WO 2004/073375 | 11/2004 |
| WO | WO 2005/100363 | * 10/2005 |
| WO | WO 2007/010007 | 1/2007 |

OTHER PUBLICATIONS

International Preliminary Report on Patentability with Written opinion and translation into English for PCT/FR2008/051697 of Apr. 8, 2010.
French Preliminary Search Report for FR 0706692 of Jul. 16, 2008.
International Search Report for PCT/FR2008/051697 of Mar. 13, 2009.

* cited by examiner

*Primary Examiner* — Nizal Chandrakumar
(74) *Attorney, Agent, or Firm* — Hueschen and Sage

(57) ABSTRACT

The present invention describes a new process for the preparation of (poly)aminoalkylaminoacetamide compounds of epipodophyllotoxin useful for their applications in therapeutics as anticancer agents. This process comprises a step of condensation of a primary-amine-containing reactant, whose amine functions are not protected, with β-chloroacetamido-4'-epipodophyllotoxin in a polar aprotic organic solvent.

16 Claims, No Drawings

PROCESS FOR THE SYNTHESIS OF ANTICANCER (POLY) AMINOALKYLAMINOACETAMIDE DERIVATIVES OF EPIPODOPHYLLOTOXIN

The present invention relates to a new process for the preparation of (poly)aminoalkylaminoacetamide derivatives of epipodophyllotoxin, of formula 1, and pharmaceutically acceptable salts thereof.

Formula 1

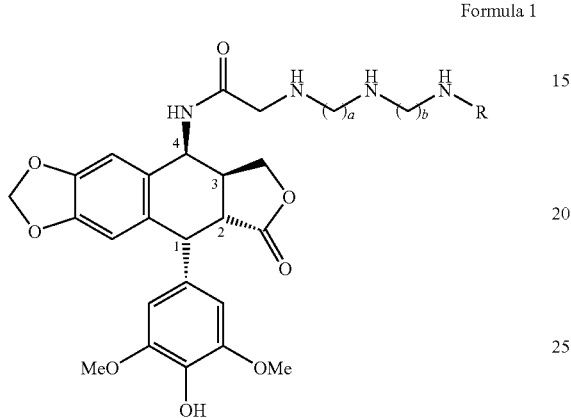

wherein R represents a hydrogen atom or a group —$(CH_2)_c$—$NH_2$, with $2 \leq a,b,c \leq 5$.

These compounds are composed of an epipodophyllotoxin-type lignan portion and a polyamine portion attached at the 4-position of the epipodophyllotoxin by way of an acetamide moiety.

The presence of the polyamine chain provides the molecule with its water solubility properties, especially for its hydrochlorides, and also its especially valuable pharmacological properties in the treatment of cancers.

These compounds, which are described in patent application WO 2005/100363, are anticancer compounds that are especially useful in the treatment of solid or non-solid tumours such as melanomas, colorectal cancers, cancers of the lung, prostate, bladder, breast, uterus, stomach, pancreas, liver and ovaries and also in the treatment of leukaemias, lymphomas and myelomas, cancers of the ENT system and brain tumours. The synthesis process described in WO 2005/100363 for the preparation of compounds of formula 1 uses, as starting material, podophyllotoxin of formula 2:

Formula 2

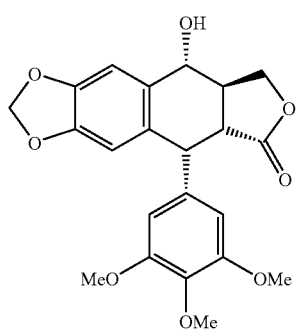

and then 4'-demethylepipodophyllotoxin of formula 3:

Formula 3

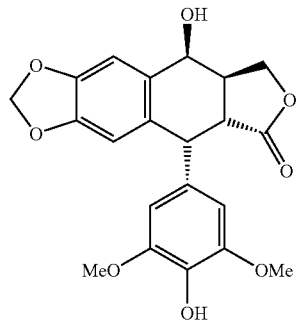

with which chloroacetonitrile is reacted in an acid medium to obtain the synthesis intermediate 4-chloroacetamido-4'-demethylepipodophyllotoxin of formula 4:

Formula 4

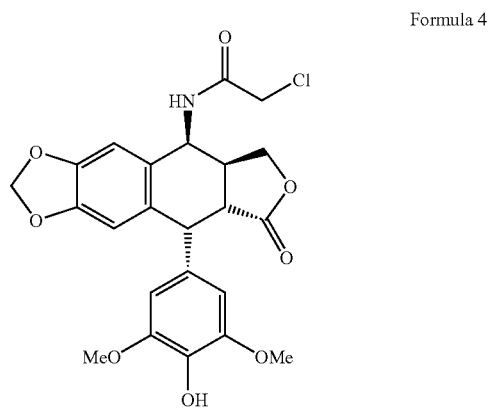

This compound is then condensed with a primary-amine-containing reactant of formula 5:

Formula 5

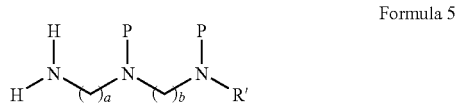

wherein R' represents a hydrogen atom or a chain —$(CH_2)_c$—NHP and wherein P represents a group protecting the amine functions.

Appropriate protecting groups may be a benzyl, benzyloxycarbonyl or tert-butyloxycarbonyl radical. This condensation is carried out in a mixture of solvents comprising a polar aprotic solvent (acetonitrile, DMF) in the presence of a Lewis base (triethylamine).

However, this process, besides the fact that it has a high number of steps and therefore quite a low overall yield, has two disadvantages:

On the one hand, the conditions used in patent specification WO 2005/100363 are conducive to epimerisation of the carbon in the 2-position of the epipodophyllotoxin derivative of formula 1, resulting in a cis-lactone form, referred to as the "picro" form, of formula 7:

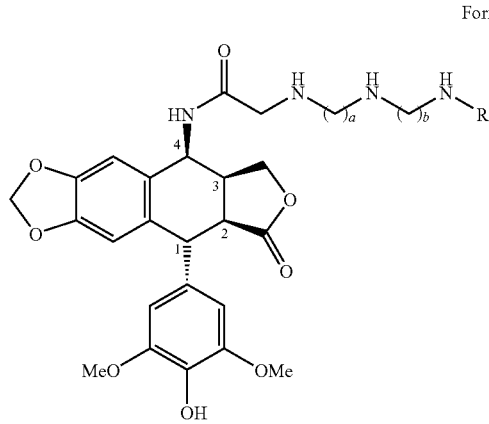

Formula 7

Purification of the desired trans-lactone product is therefore difficult and necessitates laborious and costly chromatography operations.

On the other hand, the method described hereinbefore also produces bis-alkylation type by-products, as a result of reaction of another molecule of 4β-chloroacetamido-4'-demethylepipodophyllotoxin with the product of formula 1 already formed. The use of an excess of primary-amine-containing reactant of formula 5 is then necessary for conversion of the starting materials that is as complete as possible whilst minimising the by-products obtained, which necessitates a difficult step of recovering the excess amine, making this process uneconomical.

The Applicant has found, in unexpected manner, that by using a primary-amine-containing reactant corresponding to formula 6, wherein a, b and R are as defined hereinbefore but in which the amine functions are not protected, the potential secondary products are minimised and their presence does not present a major handicap to obtaining a pure final compound.

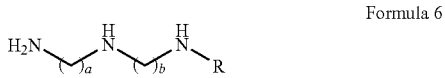

Formula 6

The direct condensation of 4-chloroacetamido-4'-demethylepipodophyllotoxin of formula 4 with the primary-amine-containing reactant, without an additional step of protecting the amine functions of the latter, is then carried out under conditions that are satisfactory in terms of yield and the purity of the product obtained. Accordingly, in the case of the compound wherein a=3, b=4 and c=3, a synthesis procedure which, when the process as described in WO 2005/100363 is employed, comprises 11 steps with an overall yield of about 15% is replaced by a synthesis procedure according to the present invention which makes it possible in only 3 steps to obtain an overall yield of 30%.

Within the framework of the synthesis procedure of the present invention, a stoichiometric amount of reagents is employed, which minimises the cost.

The preponderant product of the reaction is, then, the alkylation product forming the linear-chain compound as a result of its being very largely the primary amine function that is substituted. Such reaction selectivity is surprising in view of the secondary products obtained when using the synthesis route described in WO 2005/100363. Use of the non-protected amine results predominantly in the desired product.

This method moreover has the advantage of limiting the number of steps because of the fact that the steps for protection of the primary-amine-containing reactant are no longer necessary.

The present invention accordingly relates to a process for the synthesis of compounds of formula 1, comprising a step of condensation of the 4β-chloroacetamido-4'-demethylepipodophyllotoxin intermediate of formula 4 with a primary-amine-containing reactant of formula 6 not having prior protection of the amine functions.

The compounds of formula 1 are preferably obtained in hydrochloride form.

This condensation reaction is carried out in direct manner without its being necessary for any amine function of the primary-amine-containing reactant of formula 6 used to be protected by any suitable protecting group.

The step of condensation of 4β-chloroacetamido-4'-demethylepipodophyllotoxin of formula 4 with the non-protected primary-amine-containing reactant of formula 6 is preferably carried out in a polar aprotic solvent.

Preference is given to the polar aprotic solvent used in the condensation step being selected from: dimethylformamide, dimethylacetamide, N-methylpyrrolidone and also dimethyl sulfoxide.

Preference is also given to the condensation reaction being carried out in a temperature range between −20° C. and 30° C. inclusive. An increase in temperature is observed when the operation is conducted using an amount of several tens of grams and therefore controlling the reaction temperature is preferable. Even more preferably, the temperature will accordingly be maintained at 0° C.

The invention relates also to a process for the synthesis of compounds of formula 1 wherein the step of condensation of the 4β-chloroacetamido-4'-demethylepipodophyllotoxin intermediate of formula 4 with the primary-amine-containing reactant of formula 6 is followed by a step of recovery of compound 1.

The step of recovery of the product of formula 1 is preferably carried out by precipitation from an alcoholic solvent such as methanol or ethanol, followed by a step of reverse-phase chromatography in an acid medium. The compound is purified in an acid solution, e.g. hydrochloric acid. It is not subject to the risk of epimerisation at the lactone resulting in the "picro" derivative. Final lyophilisation makes it possible to isolate the salt of the desired compound.

Preference is also given to using, as the non-protected primary-amine-containing reactant of formula 6, spermine or spermidine of formulae 8 and 9 below.

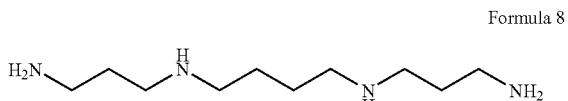

Formula 8

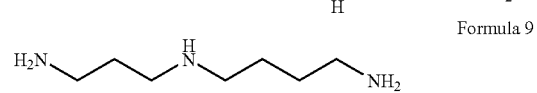

Formula 9

In the case of condensation with spermidine, which is a dissymmetrical polyamine, 2 isomeric compounds of formula 1 are obtained in equal parts (compounds wherein a=3, b=4, R=H and a=4, b=3, R=H).

In the case of condensation with spermine, it is the compound wherein a=3, b=4 and R=(CH$_2$)$_3$—NH$_2$ that is obtained.

The present invention accordingly relates also to a process for the synthesis of the compound wherein a=3, b=4 and R=H, or 2-[3-(4-aminobutylamino)-propylamino]-N-[9-(4-hydroxy-3,5-dimethoxyphenyl)-8-oxo-5,5a,6,8,8a,9-hexahydrofuro[3',4':6,7]-naphtho[2,3-d][1,3]dioxol-5-yl]-acetamide, comprising a step of condensation of 4β-chloroacetamido-4'-demethylepipodophyllotoxin of formula 4 with spermidine, followed by a step of recovery of said compound.

The present invention relates also to a process for the synthesis of the compound wherein a=4, b=3 and R=H, or 2-[4-(3-aminopropylamino)-butylamino]-N-[9-(4-hydroxy-3,5-dimethoxyphenyl)-8-oxo-5,5a,6,8,8a,9-hexahydrofuro[3',4':6,7]naphtho[2,3-d][1,3]-dioxol-5-yl]-acetamide, comprising a step of condensation of 4β-chloroacetamido-4'-demethylepipodophyllotoxin of formula 4 with spermidine, followed by a step of recovery of said compound.

The present invention relates also to a process for the synthesis of the compound wherein a=3, b=4 and R=(CH$_2$)$_3$—NH$_2$, or 2-{3-[4-(3-aminopropylamino)-butylamino]-propylamino}-N-[9-(4-hydroxy-3,5-dimethoxyphenyl)-8-oxo-5,5a,6,8,8a,9-hexahydro-furo[3',4':6,7]naphtho[2,3-d][1,3]dioxol-5-yl]-acetamide, comprising a step of condensation of 4β-chloroacetamido-4'-demethylepipodophyllotoxin of formula 4 with spermine, followed by a step of recovery of said compound.

The invention relates also to use of the primary-amine-containing reactant of formula 6 in the preparation of compounds of general formula 1 in accordance with a process involving a step of condensation between that primary-amine-containing reactant and 4β-chloroacetamido-4'-demethylepipodophyllotoxin of formula 4.

The present invention relates also to a process for the preparation of compounds of formula 1 starting from podophyllotoxin of formula 2, comprising the following steps and characterised in that the primary-amine-containing reactant used in step c) is the reactant of formula 6. The condensation of step c) is carried out in direct manner without a step of protection, by any protecting group, of the amine functions of the primary-amine-containing reactant used.
  a) Preparation of 4'-demethylepipodophyllotoxin of formula 3 starting from podophyllotoxin of formula 2
  b) Conversion of the 4'-demethylepipodophyllotoxin into 4β-chloroacetamido-4'-demethylepipodophyllotoxin of formula 4
  c) Condensation of the 4β-chloroacetamido-4'-demethylepipodophyllotoxin with a primary-amine-containing reactant of formula 6

Step a) will preferably be carried by the process described in patent application WO 97/21713, that is to say by treatment of podophyllotoxin with a pairing of strong acid/aliphatic, aromatic or functionalised sulfide in the presence of an organic or inorganic acid or in the presence of water with or without an organic water-miscible solvent.

Step b) will preferably be carried out according to the method described in patent application WO 2005/100363, that is to say by reaction of the 4'-demethylepipodophyllotoxin obtained in the preceding step, with chloroacetonitrile, in an acid medium.

Step c) and also the subsequent recovery step are carried out as described hereinbefore, the primary-amine-containing reactant used not having any protection of its amine functions.

At the end of the recovery step, the compound of general formula 1 may optionally be converted into a salt with the aid of an inorganic or organic acid.

Preference is given to carrying out the condensation step c) in a polar aprotic solvent selected from: dimethylformamide, dimethylacetamide, N-methylpyrrolidone and also dimethyl sulfoxide.

Preference is given also to the condensation reaction being carried out in a temperature range between −20° C. and 30° C. inclusive, more especially at 0° C.

Preference is given to the step of recovery of the compound of formula 1 being carried out by precipitation from an alcoholic solvent such as methanol or ethanol, followed by a step of reverse-phase chromatography in an acid medium. The compound is purified in an acid solution, e.g. hydrochloric acid.

Preference is given also to the non-protected primary-amine-containing reactant of formula 6 used in the condensation step c) being spermine or spermidine.

When it is spermidine that is used in step c), there will be obtained the two isomeric compounds of formula 1 wherein a=3, b=4, R=H and a=4, b=3, R=H in equal parts.

In the case of condensation with spermine, it is the compound wherein a=3, b=4 and R=(CH$_2$)$_3$—NH$_2$ that is obtained.

The invention relates also to use of the primary-amine-containing reactant of formula 6 in the preparation of compounds of general formula 1 starting from podophyllotoxin, in accordance with steps a) and then b) and then c) described hereinbefore.

The present invention relates also to a process for the synthesis of the compound wherein a=3, b=4 and R=H or the compound wherein a=4, b=3 and R=H, or 2-[3-(4-aminobutylamino)-propylamino]-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-acetamide or 2-[4-(3-aminopropylamino)-butylamino]-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-acetamide, comprising the following steps:
  a) Preparation of 4'-demethylepipodophyllotoxin of formula 3 starting from podophyllotoxin of formula 2
  b) Conversion of the 4'-demethylepipodophyllotoxin into 4β-chloroacetamido-4'-demethylepipodophyllotoxin of formula 4
  c) Condensation of the 4β-chloroacetamido-4'-demethylepipodophyllotoxin of formula 4 with spermidine.

These 3 steps are followed by a step of recovery of 2-[3-(4-aminobutylamino)-propylamino]-N-[9-(4-hydroxy-3,5-dimethoxyphenyl)-8-oxo-5,5a,6,8,8a,9-hexahydro-furo[3',4':6,7]naphtho[2,3-d][1,3]dioxol-5-yl]-acetamide or 2-[4-(3-aminopropylamino)-butylamino]-N-[9-(4-hydroxy-3,5-dimethoxyphenyl)-8-oxo-5,5a,6,8,8a,9-hexahydrofuro-[3',4':6,7]naphtho[2,3-d][1,3]dioxol-5-yl]-acetamide, these products being optionally converted into salts with the aid of an inorganic or organic acid.

The present invention relates also to a process for the synthesis of the compound wherein a=3, b=4 and R=(CH$_2$)$_3$—NH$_2$, or 2-{3-[4-(3-aminopropylamino)-butylamino]-propylamino}-N-[9-(4-hydroxy-3,5-dimethoxyphenyl)-8-oxo-5,5a,6,8,8a,9-hexahydrofuro[3',4':6,7]naphtho[2,3-d][1,3]dioxol-5-yl]-acetamide, comprising the following steps:
  a) Preparation of 4'-demethylepipodophyllotoxin of formula 3 starting from podophyllotoxin of formula 2
  b) Conversion of the 4'-demethylepipodophyllotoxin into 4β-chloroacetamido-4'-demethylepipodophyllotoxin of formula 4 c) Condensation of the 4β-chloroacetamido-4'-demethyl-epipodophyllotoxin of formula 4 with spermine.

followed by a step of recovery of 2-{3-[4-(3-aminopropylamino)-butylamino]-propylamino}-N-[9-(4-hydroxy-3,5-dimethoxyphenyl)-8-oxo-5,5a,6,8,8a,9-hexahydrofuro-[3',4':6,7]naphtho[2,3-d][1,3]dioxol-5-yl]-acetamide and optional conversion into a salt.

The Examples that follow illustrate the invention without limiting the scope thereof.

EXAMPLE 1

Synthesis of the compound of formula 1 wherein a=3, b=4 and c=3, or 2-{3-[4-(3-aminopropylamino)-butylamino]-propylamino}-N-[9-(4-hydroxy-3,5-dimethoxy-phenyl)-8-oxo-5,5a,6,8,8a,9-hexahydrofuro[3',4':6,7]naphtho[2,3-d][1,3]dioxol-5-yl]-acetamide, in hydrochloride form, starting from 4β-chloroacetamido-4'-demethylepipodophyllotoxin and spermine having non-protected amine functions The synthesis scheme is as follows:

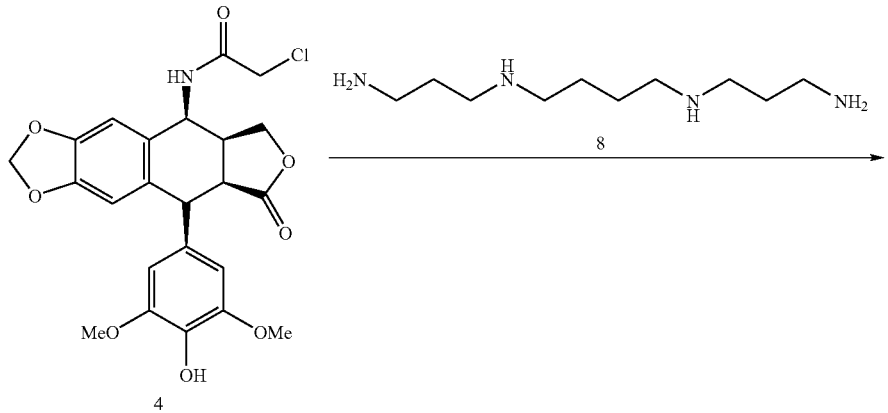

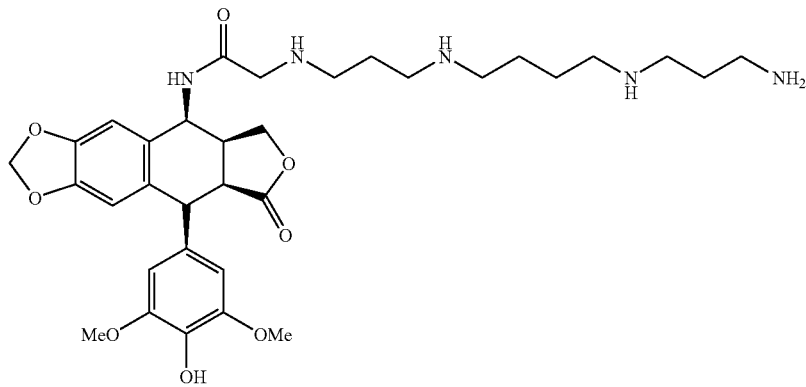

To 1 g (2.1 mmol) of 4β-chloroacetamido-4'-demethylepipodophyllotoxin, dissolved in 5 mL of DMF, there is added 0.43 g (2.1 mmol) of spermine of formula 8 in 5 mL of DMF. Stirring is maintained for 5 hours. There are then added 20 mL of EtOH, and then a solution of isopropanol/HCl is added until the pH is slightly acid. The hydrochloride precipitates out. The crystals are filtered off and dried to obtain 1.9 g of crude compound 1. Purification by preparative HPLC is carried out (Lichrospher 100 RP 18, elution HCl: c=5 mM). The fractions are lyophilised and then taken up in ethyl ether, and the hydrochloride of compound 1 is obtained in amorphous form with a purity of 97%, yield 40%.

m.p.° C.: 267° C. $^1$H NMR: (DMSO) δ 9.07 (d, 1H, J=8.32 Hz, NHCO), 8.27 (s, 1H, ArOH), 6.80 (s, 1H, $H_5$), 6.55 (s, 1H, $H_8$), 6.23 (s, 2H, $H_{2'}$, $H_{6'}$), 6.01 (d, 2H, J=12 Hz, $OCH_2O$), 5.23 (dd, 1H, J=5.3 and 8.1 Hz, $H_4$), 4.52 (d, 1H, J=5.2 Hz, $H_1$), 4.28 (t, 1H, J=8 Hz, $H_{11a}$), 3.94 (dd, 1H, J=8.8 and 10.4 Hz, $H_{11b}$), 3.8 (m, 2H, $CH_2CO$), 3.63 (s, 6H, $2xOCH_3$), 3.22 (dd, 1H, j=5 and 14.4 Hz, $H_2$), 3.06 (m, 3H, $H_3$ and $CH_2NH$), 2.99 (m, 4H, $CH_2NH$), 2.89 (m, 6H, $CH_2NH$), 2.08 (t, J=7.6 Hz, 2H, sat. $CH_2$), 1.99 (q, 2H, J=7.2 Hz, sat. $CH_2$), 1.73 (m, 4H, sat. $CH_2$). ESI-MS (m/z) 642.2 (MH+). Anal: $C_{33}H_{47}N_5O_8$, 4HCl, calc. C %, 50.32, H %, 6.53, N %, 8.89. found C %, 50.264, H %, 6.57, N %, 8.66.

EXAMPLE 2

Process for the preparation of the compound of formula 1 wherein a=3, b=4 and R=H, or 2-[3-(4-aminobutylamino)-propylamino]-N-[9-(4-hydroxy-3,5-dimethoxy-phenyl)-8-oxo-5,5a,6,8,8a,9-hexahydrofuro[3',4':6,7]naphtho[2,3-d]

[1,3]dioxol-5-yl]-acetamide hydrochloride, and the compound of formula 1 wherein a=4, b=3 and R=H, or 2-[4-(3-aminopropylamino)-butylamino]-N-[9-(4-hydroxy-3,5-dimethoxy-phenyl)-8-oxo-5,5a,6,8,8a,9-hexahydrofuro[3',4':6,7]naphtho[2,3-d][1,3]dioxol-5-yl]-acetamide, in hydrochloride form, starting from 4β-chloroacetamido-4'-demethyl-epipodophyllotoxin and spermidine having non-protected amine functions The scheme for this synthesis is as follows:

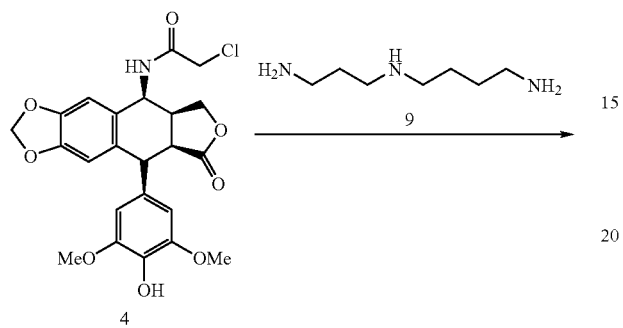

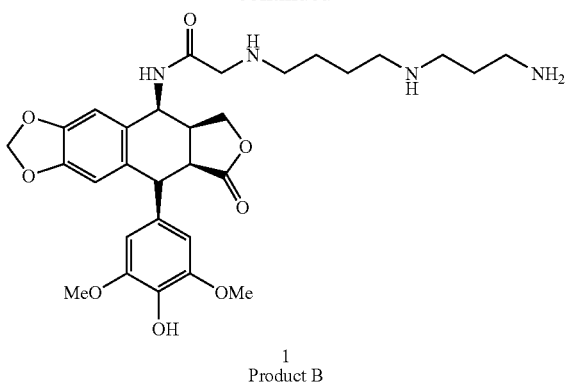

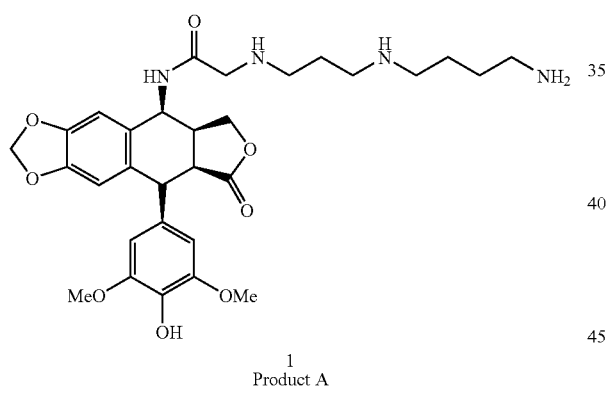

Under the same conditions as for the derivative of Example 1, but replacing the spermine by spermidine of formula 9, there are obtained the compounds of formula 1 (product A: a=3, b=4, R=H; and product B: a=4, b=3, R=H). In the same manner as in Example 1, these 2 products are isolated in equivalent proportions, with an overall yield of 40%.

These products are in all points the same as the compounds obtained in Examples 31 and 32 respectively of patent application WO 2005/100363.

These Examples 1 and 2 are transferable to the synthesis of all compounds of formula 1 by using the corresponding non-protected primary-amine-containing reactant of formula 6 instead of spermine or spermidine.

EXAMPLE 3

Synthesis of the compound of formula 1 wherein a=3, b=4 and c=3, or 2-{3-[4-(3-aminopropylamino)-butylamino]-propylamino}-N-[9-(4-hydroxy-3,5-dimethoxy-phenyl)-8-oxo-5,5a,6,8,8a,9-hexahydrofuro[3',4':6,7]naphtho[2,3-d][1,3]dioxol-5-yl]-acetamide, in hydrochloride form, starting from podophyllotoxin, in 3 steps 1st Step The synthesis scheme is as follows:

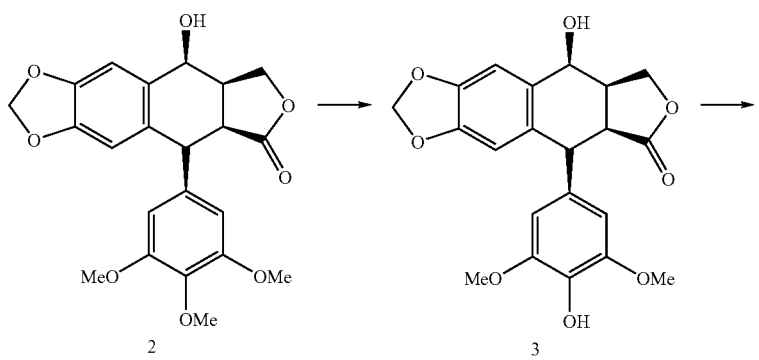

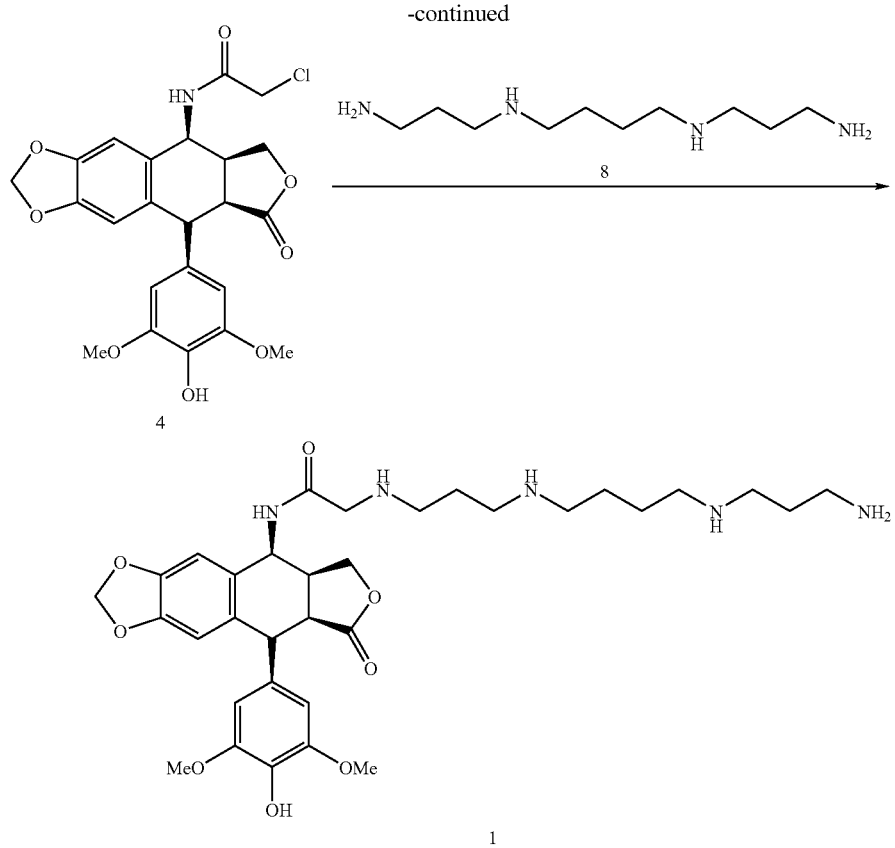

10 g (24 nmol) of podophyllotoxin are dissolved in 60 ml of trifluoroacetic acid. There are successively added 5.4 ml (72 mmol) of methanesulfonic acid. Stirring is carried out for 9 hours, 5.4 ml (72 mmol) of dimethyl sulfide are again added and stirring is carried out for 9 hours. The mixture is discharged onto ice (600 ml) and extracted with ethyl acetate (3×300 ml). The organic phases are washed with water and then with NaHCO$_3$ solution until neutral. After drying over sodium sulfate, filtration and evaporation, there are obtained 6.3 g of 4'-demethylepipodophyllotoxin, which is used directly in the next step.

2nd Step 30 g of 4'-demethylepipodophyllotoxin are added to 47.4 ml of chloroacetonitrile and then, with stirring, 3 drops of concentrated sulfuric acid are added. Stirring is carried out for 3 hours at ambient temperature. 300 ml of isopropanol are then added, with stirring. The precipitate obtained is filtered off and washed with 200 ml of isopropanol. The precipitate is rinsed with water until the pH is neutral, and then with ethyl ether. After drying in vacuo, there are obtained 34.2 g (yield 96%) of a white solid (m.p.=240° C.) corresponding to 4β-chloroacetamido-4'-demethylepipodophyllotoxin.

3rd Step

Starting from the 4β-chloroacetamido-4'-demethylepipodophyllotoxin obtained in the preceding step, synthesis is continued in accordance with the method described in Example 1 to obtain the product of formula 1 (a=3, b=4, c=3).

This Example is transferable to all compounds of formula 1 by using the corresponding non-protected primary-amine-containing reactants of formula 6.

The invention claimed is:

1. A process for the preparation of a (poly)aminoalkylaminoacetamide derivative of epipodophyllotoxin, of formula 1

Formula 1

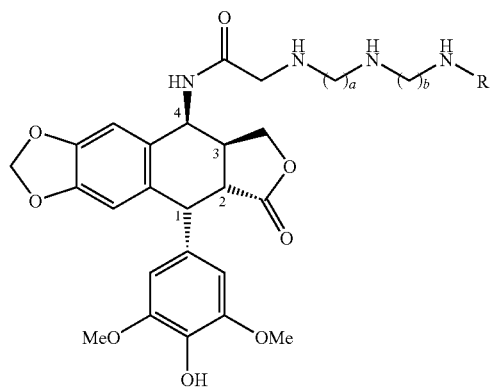

or a pharmaceutically acceptable salt thereof, wherein R represents a hydrogen atom or a group —(CH$_2$)$_c$—NH$_2$, wherein a, b and c each independently represent 2, 3, 4 or 5, comprising condensation of 4β-chloroacetamido-4'-demethylepipodophyllotoxin of formula 4

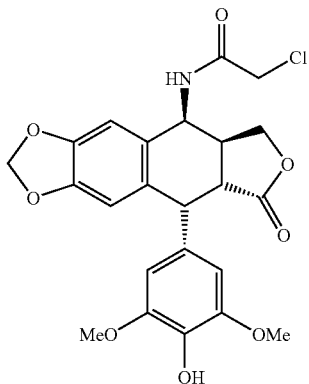

Formula 4 with a primary-amine-containing reactant of formula 6:

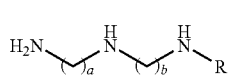

Formula 6 wherein a, b, c and R are as previously defined and wherein the amine functions have not been previously protected.

2. The process for the preparation of a (poly)aminoalkylaminoacetamide derivative of epipodophyllotoxin, of formula 1 according to claim 1, wherein the derivative is obtained as its hydrochloride salt.

3. The process according to claim 1, wherein the condensation between the 4β-chloroacetamido-4'-demethylepipodophyllotoxin and the primary-amine-containing reactant of formula 6 is carried out in a polar aprotic solvent.

4. The process according to claim 3, wherein the polar aprotic solvent is selected from dimethylformamide, dimethylacetamide, N-methylpyrrolidone and dimethyl sulfoxide.

5. The process according to claim 1, wherein the condensation between the 4β-chloroacetamido-4'-demethylepipodophyllotoxin and the primary-amine-containing reactant of formula 6 is carried out in a temperature range between −20° C. and +30° C. inclusive.

6. The process according to claim 5, wherein the condensation between the 4β-chloroacetamido-4'-demethylepipodophyllotoxin and the primary-amine-containing reactant of formula 6 is carried out at 0° C.

7. The process according to claim 1, wherein the condensation reaction between the 4β-chloroacetamido-4'-demethylepipodophyllotoxin and the primary-amine-containing reactant of formula 6 is followed by a step of recovery of the product of formula 1.

8. The process according to claim 1, wherein recovery of the compound of formula 1 is carried out by precipitation from an alcoholic solvent, followed by reverse-phase chromatography in an acid medium.

9. The process according to claim 1, wherein the primary-amine-containing reactant of formula 6 used in the step of condensation with 4β-chloroacetamido-4'-demethylepipodophyllotoxin is spermine or spermidine.

10. The process for the preparation of the compound of formula 1 wherein a represents 3, b represents 4 and c represents 3, or the compound of formula 1 is 2-{3-[4-(3-aminopropylamino)-butylamino]-propylamino}-N-[9-(4-hydroxy-3,5-dimethoxyphenyl)-8-oxo-5,5a,6,8,8a,9-hexahydrofuro[3',4':6,7]-naphtho[2,3-d][1,3]dioxol-5-yl]-acetamide, according to claim 1, comprising condensation of 4β-chloroacetamido-4'-demethylepipodophyllotoxin with spermine.

11. The process for the preparation of the compound of formula 1 wherein a represents 3, b represents 4 and R represents H, or the compound of formula 1 is 2-[3-(4-aminobutylamino)-propylamino]-N-[9-(4-hydroxy-3,5-dimethoxyphenyl)-8-oxo-5,5a,6,8,8a,9-hexahydrofuro[3',4':6,7] naphtho[2,3-d][1,3]dioxol-5-yl]-acetamide, according to claim 1, comprising condensation of 4β-chloroacetamido-4'-demethylepipodophyllotoxin of formula 4 with spermidine.

12. The process for the preparation of the compound of formula 1 wherein a represents 4, b represents 3 and R represents H, or the compound of formula 1 is 2-[4-(3-aminopropylamino)-butylamino]-N-[9-(4-hydroxy-3,5-dimethoxyphenyl)-8-oxo-5,5a,6,8,8a,9-hexahydrofuro[3',4':6,7] naphtho[2,3-d][1,3]dioxol-5-yl]-acetamide, according to claim 1, comprising condensation of 4β-chloroacetamido-4'-demethylepipodophyllotoxin of formula 4 with spermidine.

13. The process for the preparation of a compound of formula 1 according to claim 1, comprising the following steps:

a) preparation of 4'-demethylepipodophyllotoxin of formula 3

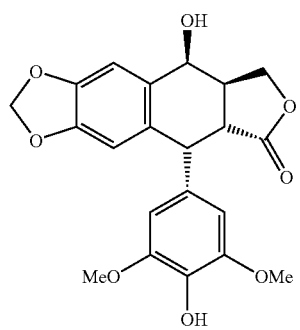

Formula 3 starting from podophyllotoxin of formula 2

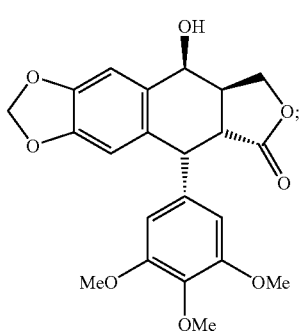

Formula 2 b) conversion of the 4'-demethylepipodophyllotoxin of formula 3 obtained in step a), into 4β-chloroacetamido-4'-demethylepipodophyllotoxin of formula 4

Formula 4

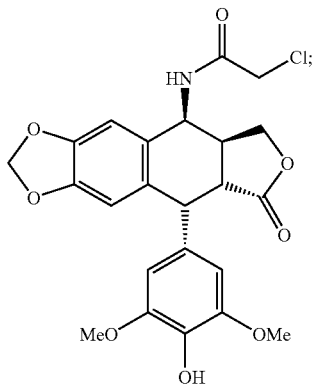

and c) condensation of the 4β-chloroacetamido-4'-demethylepipodophyllotoxin obtained in step b), with a primary-amine-containing reactant of formula 6

Formula 6

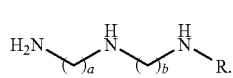

14. The process for the preparation of the compound of formula 1 wherein a represents 3, b represents 4 and c represents 3, or the compound of formula 1 is 2-{3-[4-(3-aminopropylamino)-butylamino]-propylamino}-N-[9-(4-hydroxy-3,5-dimethoxyphenyl)-8-oxo-5,5a,6,8,8a,9-hexahydrofuro[3',4':6,7]-naphtho[2,3-d][1,3]dioxol-5-yl]-acetamide, according to claim 13, comprising the following steps:

a) preparation of 4'-demethylepipodophyllotoxin starting from podophyllotoxin;

b) conversion of the 4'-demethylepipodophyllotoxin obtained in step a), into 4β-chloroacetamido-4'-demethylepipodophyllotoxin; and c) condensation of the 4β-chloroacetamido-4'-demethylepipodophyllotoxin obtained in step b), with spermine.

15. The process for the preparation of the compound of formula 1 wherein a represents 3, b represents 4 and R represents H, or the compound of formula 1 is 2-[3-(4-aminobutylamino)-propylamino]-N-[9-(4-hydroxy-3,5-dimethoxyphenyl)-8-oxo-5,5a,6,8,8a,9-hexahydrofuro[3',4':6,7] naphtho[2,3-d][1,3]dioxol-5-yl]-acetamide, according to claim 13, comprising the following steps:

a) preparation of 4'-demethylepipodophyllotoxin starting from podophyllotoxin;

b) conversion of the 4'-demethylepipodophyllotoxin obtained in step a), into 4β-chloroacetamido-4'-demethylepipodophyllotoxin; and c) condensation of the 4β-chloroacetamido-4'-demethylepipodophyllotoxin obtained in step b), with spermidine.

16. The process for the preparation of the compound of formula 1 wherein a represents 4, b represents 3 and R represents H, or the compound of formula 1 is 2-[4-(3-aminopropylamino)-butylamino]-N-[9-(4-hydroxy-3,5-dimethoxyphenyl)-8-oxo-5,5a,6,8,8a,9-hexahydrofuro[3',4':6,7] naphtho[2,3-d][1,3]dioxol-5-yl]-acetamide, according to claim 13, comprising the following steps:

a) preparation of 4'-demethylepipodophyllotoxin starting from podophyllotoxin b) conversion of the 4'-demethylepipodophyllotoxin obtained in step a), into 4β-chloroacetamido-4'-demethylepipodophyllotoxin c) condensation of the 4β-chloroacetamido-4'-demethylepipodophyllotoxin obtained in step b), with spermidine.

* * * * *